US011351152B2

(12) United States Patent
Mukunda et al.

(10) Patent No.: US 11,351,152 B2
(45) Date of Patent: Jun. 7, 2022

(54) METHOD AND COMPOSITION FOR TREATING SEIZURE DISORDERS

(71) Applicant: India Globalization Capital, Inc., Bethesda, MD (US)

(72) Inventors: Ramachandra Mukunda, Potomac, MD (US); Ranga Chelva Krishna, Englewood, NJ (US)

(73) Assignee: India Globalization Capital, Inc., Potomac, MD (US)

( * ) Notice: Subject to any disclaimer, the term of this patent is extended or adjusted under 35 U.S.C. 154(b) by 0 days.

(21) Appl. No.: 16/308,837

(22) PCT Filed: Jun. 14, 2017

(86) PCT No.: PCT/US2017/037394
§ 371 (c)(1),
(2) Date: Dec. 11, 2018

(87) PCT Pub. No.: WO2017/218629
PCT Pub. Date: Dec. 21, 2017

(65) Prior Publication Data
US 2020/0179342 A1  Jun. 11, 2020

Related U.S. Application Data

(60) Provisional application No. 62/350,215, filed on Jun. 15, 2016.

(51) Int. Cl.
| A61K 31/4166 | (2006.01) |
| A61K 31/05 | (2006.01) |
| A61K 31/07 | (2006.01) |
| A61K 31/122 | (2006.01) |
| A61K 31/355 | (2006.01) |
| A61K 31/519 | (2006.01) |
| A61K 31/593 | (2006.01) |
| A61K 31/714 | (2006.01) |

(52) U.S. Cl.
CPC .......... *A61K 31/4166* (2013.01); *A61K 31/05* (2013.01); *A61K 31/07* (2013.01); *A61K 31/122* (2013.01); *A61K 31/355* (2013.01); *A61K 31/519* (2013.01); *A61K 31/593* (2013.01); *A61K 31/714* (2013.01)

(58) Field of Classification Search
CPC ..... A61K 31/4166; A61K 31/05; A61K 31/07
See application file for complete search history.

(56) References Cited

U.S. PATENT DOCUMENTS

| 5,240,937 A | 8/1993 | Kelley |
| 5,391,740 A | 2/1995 | Wang et al. |
| 6,503,532 B1 | 1/2003 | Murty |
| 6,683,086 B2 | 1/2004 | Druzgala et al. |
| 6,949,582 B1 | 9/2005 | Wallace |
| 8,859,540 B2 | 10/2014 | Rundfeldt et al. |
| 9,095,554 B2 | 8/2015 | Lewis et al. |
| 10,111,840 B2 | 10/2018 | Guy et al. |
| 10,117,891 B2 | 11/2018 | Mukunda et al. |
| 10,596,159 B2 | 3/2020 | Mukunda et al. |
| 10,709,671 B2 | 7/2020 | Guy et al. |
| 10,729,665 B2 | 8/2020 | Whalley et al. |
| 10,751,300 B2 | 8/2020 | Mukunda et al. |
| 10,933,082 B2 | 3/2021 | Mukunda et al. |
| 2004/0043043 A1 | 3/2004 | Schlyter et al. |
| 2004/0138293 A1 | 7/2004 | Werner et al. |
| 2005/0042172 A1 | 2/2005 | Whittle |
| 2006/0127499 A1 | 6/2006 | Lazarev et al. |
| 2006/0257502 A1 | 11/2006 | Liu |
| 2007/0293440 A1 | 12/2007 | Smith-Swintosky et al. |
| 2007/0293476 A1 | 12/2007 | Smith-Swintosky et al. |
| 2008/0254017 A1 | 10/2008 | Kane et al. |
| 2010/0035978 A1 | 2/2010 | Guy et al. |
| 2010/0292345 A1 | 11/2010 | Pertwee |
| 2011/0065627 A1 | 3/2011 | Barathur |
| 2011/0217278 A1 | 9/2011 | Felder |
| 2011/0301238 A1 | 12/2011 | Borges |
| 2012/0004251 A1 | 1/2012 | Whalley et al. |
| 2012/0165402 A1 | 6/2012 | Whalley et al. |
| 2012/0322782 A1 | 12/2012 | Narishetty et al. |
| 2013/0065898 A1 | 3/2013 | Rundfeldt et al. |
| 2013/0296398 A1 | 11/2013 | Whalley et al. |
| 2013/0309306 A1 | 11/2013 | Rogawski et al. |
| 2014/0050789 A1 | 2/2014 | Bogawski et al. |
| 2014/0155456 A9 | 6/2014 | Whalley et al. |
| 2014/0243405 A1 | 8/2014 | Whalley et al. |
| 2014/0348926 A1 | 11/2014 | Hoffman et al. |

(Continued)

FOREIGN PATENT DOCUMENTS

| CA | 2424356 A | 4/2003 |
| GB | 2471523 A | 1/2011 |

(Continued)

OTHER PUBLICATIONS

Sesame seeds (Sesame seeds nutrition facts and health benefits; https://www.nutrition-and-you.com/sesame-seeds.html, downloaded on Aug. 31, 2020).*
Dietary Supplement Ingredient Database (https://dsid.od.nih.gov/Conversions.php; downloaded on Sep. 20, 2021).*
U.S. Appl. No. 16/148,775, filed Oct. 1, 2018 (pending) (copy readily available from the USPTO records).
Office Actions dated May 15, 2018 and Jan. 18, 2019 in U.S. Appl. No. 15/104,556, filed Jun. 16, 2016 (pending) (copy readily avaiable from the USPTO records).
Leo, Lowe (Potentiation of Ethanol-Induced Hepatic Vitamin A Depletion by Phenobarbital and Butylated Hydroxytoluene, Jan. 1987, Abstract Only).
Okusaka (Phase I and pharmacokinetic clinical trial of oral administration of the acyclic retinoid NIK-333, Apr. 2011, Abstract only).

(Continued)

*Primary Examiner* — Pancham Bakshi
(74) *Attorney, Agent, or Firm* — Studebaker & Brackett PC

(57) ABSTRACT

A composition for treating seizure disorders such as epilepsy comprises (i) an anticonvulsant drug of the hydantoin family; (ii) phytocannabinoid cannabidiol (CBD); and (iii) a fat-soluble vitamin.

26 Claims, No Drawings

(56) References Cited

U.S. PATENT DOCUMENTS

| | | |
|---|---|---|
| 2015/0086494 A1 | 3/2015 | Sekura et al. |
| 2015/0265637 A1 | 9/2015 | Kane et al. |
| 2015/0335590 A1 | 11/2015 | Whalley et al. |
| 2015/0359756 A1 | 12/2015 | Guy et al. |
| 2017/0027978 A1 | 2/2017 | Mukunda et al. |
| 2017/0273913 A1 | 9/2017 | Whalley et al. |
| 2018/0028489 A1* | 2/2018 | Vangara ............ A61K 2300/00 |
| 2018/0161285 A1 | 6/2018 | Mukunda et al. |
| 2018/0228788 A1 | 8/2018 | Mukunda et al. |
| 2019/0030062 A1 | 1/2019 | Mukunda et al. |
| 2019/0247324 A1 | 8/2019 | Whalley et al. |
| 2020/0009067 A1 | 1/2020 | Hoffman et al. |
| 2020/0046722 A1 | 2/2020 | Mukunda |
| 2020/0179342 A1 | 6/2020 | Mukunda et al. |
| 2020/0383935 A1* | 12/2020 | Mukunda ............... A61K 31/05 |
| 2021/0023053 A1 | 1/2021 | Mukunda et al. |

FOREIGN PATENT DOCUMENTS

| | | |
|---|---|---|
| GB | 2471565 A | 1/2011 |
| GB | 2485291 A | 5/2012 |
| WO | WO 2001/00196 A2 | 1/2001 |
| WO | WO 02/064109 A2 | 8/2002 |
| WO | WO 2004/075896 A1 | 9/2004 |
| WO | WO 2010/048423 A1 | 4/2010 |
| WO | 2011/001169 A1 | 1/2011 |
| WO | WO 2011/063164 A2 | 5/2011 |
| WO | WO 2011/110866 A1 | 9/2011 |
| WO | 2012/093255 A1 | 7/2012 |
| WO | 2013/108254 A1 | 7/2013 |
| WO | WO 2014/145490 A2 | 9/2014 |
| WO | WO 2016/044370 A1 | 3/2016 |
| WO | 2016/059403 A1 | 4/2016 |
| WO | WO 2016/059399 A1 | 4/2016 |
| WO | WO 2016/118391 A1 | 7/2016 |
| WO | WO 2016/160542 A1 | 10/2016 |
| WO | WO 2017/027651 A1 | 2/2017 |
| WO | WO 2017/218629 A1 | 12/2017 |
| WO | WO 2018/160510 A1 | 9/2018 |

OTHER PUBLICATIONS

International Application S.N. PCT/US2018/019814, filed Feb. 27, 2018 (pending) (copy readily available from the USPTO records).
PCT Search Report dated Apr. 20, 2018 in International App. S.N. PCT/US2018/019814, filed Feb. 27, 2018 (11 pages).
U.S. Appl. No. 15/751,901, filed Feb. 12, 2018 (pending) (copy readily available from the USPTO records).
Office Actions dated Nov. 26, 2018 in U.S. Appl. No. 15/751,901, filed Feb. 12, 2018 (pending) (copy readily available from the USPTO records).
U.S. Appl. No. 15/104,556, filed Jun. 15, 2016 (pending).
International Application S.N. PCT/US2017/037394, filed Jun. 14, 2017 (pending) (copy can be readily accessed from the PTO records).
PCT Search Report dated Dec. 10, 2015, in International App. S.N. PCT/US2015/050342, filed Sep. 16, 2015 (9 pages).
PCT Search Report dated Mar. 16, 2016, in International App. S.N. PCT/US2016/013323, filed Jan. 14, 2016 (8 pages).
PCT Search Report dated Jun. 17, 2016, in International App. S.N. PCT/US2016/24145, filed Mar. 25, 2016 (10 pages).
PCT Search Report dated Oct. 31, 2016, in International App. S.N. PCT/US2016/46451, filed Aug. 11, 2016 (9 pages).
PCT Search Report dated Aug. 31, 2017, in International App. S.N. PCT/US2017/037394, filed Jun. 14, 2017 (10 pages).
Siemens et al., Effect of cannabis on pentobarbital-induced sleeping time and pentobarbital metabolism in the rat, Biochemical Pharmacology, vol. 23: 477-488, 1974 [retrieved on Feb. 25, 2016]. Retrieved from the internet :<URL: http://www.sciencedirect.com/science/article/pii/0006295274906121>abstract.
Schlanger, S et al., Diet Enriched with Omega-3 Fatty Acids Alleviates Convulsion Symptoms in Epilepsy Patients. Epilepsia. 2002. vol. 43. No. 1; abstract; p. 103; first-second columns: p. 104, first column.
McMahan, K. Hemp Seed Oil—Why Should We Use It? Monterey Bay Hollistic Alliance. 2014; https://montereybayhollistic.wordpress.com/2014/08123/hemp-seed-oil/; pp. 1-2, 4.
Kardinal. CG et al. Controlled trial of cyproheptadine in cancer patients with anorexia and/or cachexia. Cancer. Jun. 15, 1990. vol. 65. pp. 2657-2662; abstract; p. 2659. left column, 2nd, 4th paragraphs; p. 2661, right column, 2nd paragraph; table 5.
Abbvie Inc. "MARINOL (dronabinol) capsules prescribing information" Reference ID: 4145204; Aug. 2017; https://www.accessdata.fda.gov/drugsatfda_docs/label/2017/018651s029lbl.pdf, 20 pages.
Amin & Ali "Pharmacology of medical cannabis" Adv Exp Med Biol; Jul. 2019; 1162: 151-165.
Anderson et al. "Coadministered cannabidiol and clobazam: Preclinical evidence for both pharmacodynamic and pharmacokinetic interactions" Epilepsia; Oct. 2019; 60(11): 2224-2234.
Antilla & Leinonen "A review of the pharmacological and clinical profile of mirtazapine" CNS Drug Rev; Jun. 2006; 7(3): 249-264.
Ayano "Psychotropic medications metabolized by cytochromes P450 (CYP) 2D6 enzyme and relevant drug interactions" Clin Pharmacol Biopharm; Sep. 2016; 5(4): 162. doi: 10.4172/2167-065X.1000162, four pages.
Bergamaschi et al. "Safety and side effects of cannabidiol, a Cannabis sativa constituent" Curr Drug Saf; Sep. 2011; 6(4): 237-249.
Bergmann et al. "Clinical trial simulations of the interaction between cannabidiol and clobazam and effect on drop-seizure frequency" Br J Clin Pharmacol; Feb. 2020; 86(2): 380-385.
Boggs et al. "Clinical and preclinical evidence for functional interactions of cannabidiol and Δ9-tetrahydrocannabinol" Neuropsychopharmacol; Jan. 2018 ePub Oct. 2017; 43(1): 142-154.
Bornheim & Correia "Effect of cannabidiol on cytochrome P-450 isozymes" Biochem Pharmacol; Sep. 1989; 38(17): 2789-2794.
Brown & Winterstein "Potential adverse drug events and drug-drug interactions with medical and consumer cannabidiol (CBD) use" J Clin Med; Jul. 2019; 8(7): 989; doi:10.3390/jcm8070989, 14 pages.
Buchanan-Peart et al. "Cannabis, more than the euphoria: Its therapeutic use in drug-resistant epilepsy" Jul. 2020; 12(7): e9299, doi: 10.7759/cureus.9299, eight pages.
Capasso "Do cannabinoids confer neuroprotection against epilepsy? An overview" Open Neurol J; Dec. 2017; 11: 61-73.
Chang "Cannabidiol and serum antiepileptic drug levels: The ABCs of CBD With AEDs" Epilepsy Curr; Jan.-Feb. 2018; 18(1): 33-34.
Cilio et al. "The case for assessing cannabidiol in epilepsy" Epilepsia; May 2014; 55(6): 787-790.
Consroe & Wolkin "Cannabidiol—Antiepileptic drug comparisons and interactions in experimentally induced seizures in rats" J Pharmacol Exp Ther; Apr. 1977; 201(1): 26-32. The attached is more legible than the copy the Examiner previously considered.
Contin et al. "Cannabidiol in pharmacoresistant epilepsy: Clinical pharmacokinetic data from an expanded access program" Front Phamacol; Mar. 2021; 12: 637801, doi: 10.3389/fphar.2021.637801, seven pages.
Corcos & Lagadic-Gossmann "Gene induction by phenobarbital: An update on an old question that receives key novel answers" Pharmacol Toxicol; Sep. 2001; 89(3): 113-122.
Czekaj "Phenobarbital-induced expression of cytochrome P450 genes" Acta Biochim Pol; Feb. 2000; 47(4): 1093-1105.
Devinsky et al. "Cannabidiol: Pharmacology and potential therapeutic role in epilepsy and other neuropsychiatric disorders" Epilepsia; Jun. 2014 ePub May 2014; 55(6): 791-802.
Devinsky et al. "Cannabidiol efficacy independent of clobazam: Meta-analysis of four randomized controlled trials" Acta Neurol Scand; Dec. 2020; 142(6): 531-540.
Devitt-Lee "Pot is hot—What you need to know" Sonoma Med; Oct. 2017; 68(4): 33-48.
Devitt-Lee "A primer on cannabinoid-drug interactions" www.projectcbd.org/sites/projectcbd/files/downloads/cannabinoid-drug-interactions_2018-10-11.pdf; Sep. 2018, updated Jan. 2019; 35 pages.

(56) References Cited

OTHER PUBLICATIONS

Epilepsy Society "Phenobarbital" 2014; https://www.epilepsysociety.org.uk/phenobarbital#.XmaHcDbrufA_; two pages.
Fasinu et al. "Current status and prospects for cannabidiol preparations as new therapeutic agents" Pharmacotherapy; Jul. 2016; 36(7): 781-796.
Franco & Perucca "Pharmacological and therapeutic properties of cannabidiol for epilepsy drugs" Drugs; Sep. 2019; 79(13): 1435-1454.
Gaston et al. "Interactions between cannabidiol and commonly used antiepileptic drugs" Epilepsia; Sep. 2017; 58(9): 1586-1592.
Gauthier & Mattson "Clobazam: A safe, efficacious, and newly rediscovered therapeutic for epilepsy" CNS Neurosci Ther; Jul. 2015 ePub Apr. 2015; 21(7): 543-548.
Geffrey et al. "Drug-drug interaction between clobazam and cannabidiol in children with refractory epilepsy" Epilepsia; Aug. 2015 ePub Jun. 2015; 56(8): 1246-1251.
Giacoppo et al. "Cannabinoids: New promising agents in the treatment of neurological diseases" Molecules; Nov. 2014; 19(11): 18781-18816, doi: 10.3390/molecules191118781.
Greenwich Biosciences, Inc. "EPIDIOLEX (cannabidiol) capsules prescribing information" Reference ID: 4282447; Jun. 2018; https://www.accessdata.fda.gov/drugsatfda_docs/label/2018/210365lbl.pdf, 30 pages.
Gülck & Møller "Phytocannabinoids: Origins and biosynthesis" Trends Plant Sci; Oct. 2020 ePub Jul. 2020; 25(10): 985-1004.
Gunning et al. "Cannabidiol in conjunction with clobazam: Analysis of four randomized controlled trials" Acta Neurol Scand; Feb. 2021; 143(2): 154-163.
Hill et al. "Δ9-Tetrahydrocannabivarin suppresses in vitro epileptiform and in vivo seizure activity in adult rats" Epilepsia; Aug. 2010; 51(8): 1522-1532.
Hoffelt & Gross "A review of significant pharmacokinetic drug interactions with antidepressants and their management" Ment Health Clin; May 2016 ePub Jan. 2016; 6(1): 35-41, doi: 10.9740/mhc.2016.01.035.
Hollo et al. "Correction of vitamin D deficiency improves seizure control in epilepsy: A pilot study" Epilepsy Behav; Apr. 2012; 24(1): 131-133.
Hosseinpour et al. "Phenobarbital suppresses vitamin D3 25-hydroxylase expression: A potential new mechanism for drug-induced osteomalacia" Biochem Biophys Res Commun; Jun. 2007; 357(3): 603-607.
Hunt & Jones "Tolerance and disposition of tetrahydrocannabinol in man" J Pharmacol Exp Ther; Nov. 1980; 215(1): 35-44.
Huntsman et al. "Dosage related efficacy and tolerability of cannabidiol in children with treatment-resistant epileptic encephalopathy: Preliminary results of the CARE-E study" Front Neurol; Jul. 2019; 10: 716, doi: 10.3389/fneur.2019.00716, nine pages.
Iffland & Grotenhermen "An update on safety and side effects of cannabidiol: A review of clinical data and relevant animal studies" Cannabis Cannabinoid Res; Jun. 2017; 2(1): 139-154.
Ilangaratne et al. "Phenobarbital: Missing in action" Bull World Health Org; Dec. 2012; 90(12): 871-871A.
Insys Therapeutics, Inc. "SYNDROS (dronabinol) oral solution" Reference ID: 4103077; May 2017; https://www.accessdata.fda.gov/drugsatfda_docs/label/2017/205525s003lbl.pdf, 27 pages.
Johannessen & Landmark "Antiepileptic drug interactions—Principles and clinical implications" Curr Neuropharmacol; Sep. 2010; 8(3): 254-267.
Jones et al. "Cannabidiol displays antiepileptiform and antiseizure properties in vitro and in vivo" J Pharmacol Exp Ther; Feb. 2010; 332(2): 569-577.
Jones et al. "Cannabidiol exerts anti-convulsant effects in animal models of temporal lobe and partial seizures" Seizure; Jun. 2012; 21(5): 344-352.
Kardinal et al. "Controlled trial of cyproheptadine in cancer patients with anorexia and/or cachexia" Cancer; Jun. 1990; 65(12): 2657-2662. The attached is more legible than the copy the Examiner previously considered.
Kimura et al. "Δ9-Tetrahydrocannabinol, a major marijuana component, enhances the anesthetic effect of pentobarbital through the CB1 receptor" Forensic Toxicol; Jan. 2019 ePub Nov. 2018; 37: 207-214.
Kocis & Vrana "Delta-9-tetrahydrocannabinol and cannabidiol drug-drug interactions" Med Cannabis Cannabinoids Aug. 2020 ePub Jul. 2020; 3(1): 61-73.
Lattanzi et al. "Highly purified cannabidiol for epilepsy treatment: A systematic review of epileptic conditions beyond Dravet syndrome and Lennox-Gastaut syndrome" Curr Drug Saf; Sep. 2011; 35(3): 265-281.
Laux et al. "Long-term safety and efficacy of cannabidiol in children and adults with treatment resistant Lennox-Gastaut syndrome or Dravet syndrome: Expanded access program results" Epilepsy Res; Aug. 2019; 154: 13-20.
Leo et al. "Potentiation of ethanol-induced hepatic vitamin A depletion by phenobarbital and butylated hydroxytoluene" J Nutr; Jan. 1987; 117(1): 70-76, abstract only. The attached is more legible than the copy the Examiner previously considered.
Lim et al. "A systematic review of the effectiveness of medical cannabis for psychiatric, movement and neurodegenerative disorders" Clin Psychopharmcol Neurosci; Nov. 2017; 15(4): 301-312.
Lucas et al. "The pharmacokinetics and the pharmacodynamics of cannabinoids" Br J Clin Pharmcol; Nov. 2018 ePub Aug. 2018; 84(11): 2477-2482.
Mannucci et al. "Neurological aspects of medical use of cannabidiol" CNS Neurol Disord Drug Targets; Aug. 2017; 16(5): 541-553.
McMahan "Hemp seed oil—Why should we use it?" Monterey Bay Hollistic Alliance; 2014; montereybayhollistic.wordpress.com/2014/08/23/hemp-seed-oil/; six pages. The attached is more legible than the copy the Examiner previously considered.
Millar et al. "A systematic review on the pharmacokinetics of cannabidiol in humans" Front Pharmcol; Nov. 2018; 9: 1365, doi: org/10.3389/fphar.2018.01365, 13 pages.
Millar et al. "A systematic review of cannabidiol dosing in clinical populations" Br J Clin Pharmacol; Sep. 2019 ePub Jul. 2019; 85(9): 1888-1900.
Miziak et al. "Drug-drug interactions between antiepileptics and cannabinoids" Expert Opin Drug Metab Toxicol; Apr. 2019; 15(5): 407-415.
Morano et al. "Cannabinoids in the treatment of epilepsy: Current status and future prospects" Neuropsychiatr Dis Treat; Feb. 2020; 16: 381-396.
Morrison et al. "A phase 1, open-label, pharmacokinetic trial to investigate possible drug-drug interactions between clobazam, stiripentol, or valproate and cannabidiol in healthy subjects" Clin Pharmacol Drug Dev; Nov. 2019; 8(8): 1009-1031.
Ochoa "What is the role of phenobarbital in the treatment of epilepsy?" Medscape; Jan. 2020; www.medscape.com/answers/1187334-187109/what-is-the-role-of-phenobarbital-in-the-treatment-of-epilepsy; two pages.
Okusaka et al. "Phase I and pharmacokinetic clinical trial of oral administration of the acyclic retinoid NIK-333" Hepatol Res; Apr. 2011; 41(6): 542-552, abstract only. The attached is more legible than the copy the Examiner previously considered.
Paton & Pertwee "Effect of cannabis and certain of its constituents on pentobarbitone sleeping time and phenazone metabolism" Br J Pharmcol; Feb. 1972; 44(2): 250-261.
Patra et al. "Cannabidiol reduces seizures and associated behavioral comorbidities in a range of animal seizure and epilepsy models" Epilepsia; Feb. 2019; 60(2): 303-314.
Patra et al. "Cannabidiol improves survival and behavioural co-morbidities of Dravet syndrome in mice" Br J Pharmacol; Jun. 2020; 177(12): 2779-2792.
Patsalos "Antiepileptic Drug Interactions—A Clinical Guide" Cham, Switzerland: Springer International Publishing; Feb. 2016; iii-xIix.
Patsalos et al. "Clinical implications of trials investigating drug-drug interactions between cannabidiol and enzyme inducers or inhibitors or common antiseizure drugs" Epilepsia; Sep. 2020; 61(9): 1854-1868.

(56) References Cited

OTHER PUBLICATIONS

Perry "Don't fear the reefer—Evidence mounts for plant-based cannabidiol as teatment for epilepsy" Epilepsy Curr; Mar.-Apr. 2019; 19(2): 93-95.
Perucca "An introduction to antiepileptic drugs" Epilepsia; Jun. 2005; 45(suppl 4): 31-37.
Perucca "Clinically relevant drug interactions with antiepileptic drugs" Br J Clin Pharmacol; Mar. 2006; 61(3): 246-255.
Perucca "Drug interactions in epilepsy" Arq Neuropsiquiatr; Dec. 1980; 38(4): 331-340.
Perucca "Cannabinoids in the treatment of epilepsy: Hard evidence at last?" J Epilepsy Res; Dec. 2017; 7(2): 61-76.
Rahim et al. "Experimental theapeutic strategies in epilepsies using anti-seizure medications" J Exp Pharmcol; Mar. 2021; 13: 265-290.
Raucci et al. "Cannabidiol treatment for refractory epilepsies in pediatrics" Front Pharmacol; Sep. 2020; 11: 586110, doi: 10.3389/fphar.2020.586110, ten pages.
Rocha et al. "Is cannabidiol a drug acting on unconventional targets to control drug-resistant epilepsy?" Epilepsia Open; Jan. 2020; 5(1): 36-49.
Rosenberg et al. "Therapeutic effects of cannabinoids in animal models of seizures, epilepsy, epileptogenesis, and epilepsy-related neuroprotection" Epilepsy Behav; May 2017; 70(part B): 319-327.
Dos Santos et al. "Phytocannabinoids and epilepsy" J Clin Pharm Ther; Apr. 2015; 40(2): 135-143.
Schlanger et al. "Diet enriched with omega-3 fatty acids alleviates convulsion symptoms in epilepsy patients" Epilepsia; Jan. 2002; 43(1): 103-104. The attached is more legible than the copy the Examiner previously considered.
Sheehan et al. "The effect of β-carotene supplementation on the pharmacokinetics of nelfinavir and its active metabolite M8 in HIV-1-infected patients" Molecules; Jan. 2012; 17(1): 688-702.
Siemens et al. "Effect of cannabis on pentobarbital-induced sleeping time and pentobarbital metabolism in the rat" Biochem Pharmacol; Feb. 1974; 23(3): 477-488, abstract only. The attached is more legible than the copy the Examiner previously considered.
Silva et al. "Cannabidiol in the treatment of epilepsy: A focused review of evidence and gaps" Front Neurol; Oct. 2020; 11: 531939, doi: 10.3389/fneur.2020.531939, six pages.
Silvestro et al. "Use of cannabidiol in the treatment of epilepsy: Efficacy and security in clinical trials" Molecules; Apr. 2019; 24(8): 1459, doi: 10.3390/molecules24081459, 25 pages.
Solvay Pharmaceuticals, Inc. "MARINOL (dronabinol) capsules" NDA 18-651/S-021; Sep. 2004; https:J/www.accessdata.fda.gov/drugsatfda_docs/label/2005/018651s021lbl.pdf, 11 pages.
Strzelczyk & Schubert-Bass "Expanding the treatment landscape for Lennox-Gastaut syndrome: Current and future strategies" CNS Drugs; Jan. 2021; 35(1): 61-83.
Szarflarski et al. "Long-term safety and treatment effects of cannabidiol in children and adults with treatment-resistant epilepsies: Expanded access program results" Epilepsia; Aug. 2018 ePub Jul. 2018; 59(8): 1540-1548.
Szarflarski et al. "Cannabidiol improves frequency and severity of seizures and reduces adverse events in an open-label add-on prospective study" Epilepsy Behav; Oct. 2018 ePub Aug. 2018; 87: 131-136.
Thakur et al. "Natural cannabinoids: Templates for drug discovery" Life Sci; Dec. 2005 ePub Oct. 2005; 78(5): 454-166.
Valeant Pharmaceuticals "CESAMET (nabilone)) capsules" NDA 18-677/S-011; May 2006; https://www.accessdata.fda.gov/drugsatfda_docs/label/2006/018677s0111bl.pdf,11 pages.
Vega-Garcia al. "Cannabinoids: A new perspective on epileptogenesis and seizure treatment in early life in basic and clinical studies" Front Behav Neurosci; Jan. 2021; 14: 610484, doi: 10.3389/fnbeh.2020.610484, 18 pages.
Vossler et al. "Summary of antiepileptic drugs available in the United States of America" Curr Rev Clin Sci; Jul. 2018; 18(4 suppl 1): 1-25.
Von Wrede et al. "Cannabidiol in the treatment of epilepsy" Clin Drug Invest; Mar. 2021; 41(3): 211-220.
Waxman & Azaroff "Phenobarbital induction of cytochrome P-450 gene expression" Biochem J; Feb. 1992; 281 (pt 3): 577-592.
Zaccara & Perucca "Interactions between antiepileptic drugs, and between antiepileptic drugs and other drugs" Epileptic Disord; Dec. 2014; 16(4): 409-431.
Zavala-Tecuapetla et al. "Insights into potential targets for therapeutic intervention in epilepsy" Int J Mol Sci; Nov. 2020; 21(22): 8573, doi: 10.3390/ijms21228573, 54 pages.
Zhornitsky & Potvin "Cannabidiol in humans—The quest for therapeutic targets" Pharmaceuticals (Basel); May 2012; 5(5): 529-552.

* cited by examiner

METHOD AND COMPOSITION FOR TREATING SEIZURE DISORDERS

CROSS-REFERENCE TO RELATED APPLICATIONS

This application is the national stage of International Application No. PCT/US2017/037394, filed Jun. 14, 2017; which claims priority from U.S. Provisional Application No. 62/350,215, filed Jun. 15, 2016, which is hereby incorporated herein in its entirety by reference.

FIELD AND BACKGROUND OF THE INVENTION

This invention relates to compositions and methods for treating multiple types of seizure disorders and epilepsy in humans and animals (mammals) using a combination of phytocannabinoid cannabidiol (CBD), a hydantoin anticonvulsant drug and a P450 blocking compound such as vitamins A, D, E and K.

About 50 million people worldwide are affected by Epilepsy (Sander, 2003). Epilepsy is due to multiple factors including Sodium, Potassium, GABA and NMDA. Modulating one or more of these receptors are required to maximally control epilepsy. It is believed that mono therapy is adequate in up to 25 percent of patients.

The use of CBD in combination with standard anti-epileptic drug (SAED) that act via sodium or calcium channels for the treatment of Epilepsy is described in US patent Application US 2013/0296398 A1.

Several researchers have suggested that *Cannabis*-based medicines may have the potential to treat hyper excitability in the central nervous system (Wingerchuk 2004, Alger, 2006)

Consroe et al. in 1975 described the case of a young man for whom the standard treatment of phenobarbital and phenytoin did not control his seizures. When the young man smoked *Cannabis* he had no seizures. They concluded that *Cannabis* might have anticonvulsant effects on human epilepsy.

In 1990 a study by Ng involving a population of 308 epileptic patients showed that the use of *Cannabis* reduced seizures. However, the study was later criticized in a report in the Institute of Medicine (1999) that claimed health status prior to hospital admissions may have been a factor that influenced their drug use rather than the other way around.

In 1980 Cunha et al., reported that patients that were administered 200-300 mg of cannabidiol in combination with regular medication showed improvement over those that received a placebo. Mild sedation was reported as an unwanted side effect.

In 1986 Ames reported a study in which 12 epileptic patients were given 200-300 mg of cannabidiol per day in combination with standard antiepileptic drugs with no significant improvement in seizure frequency.

In 1990 Trembly et al reported that 900-1200 mg of cannabidiol a day for 10 months markedly reduced the frequency of seizures in the single patient that they tested.

In addition to reports that suggest that CBD may be beneficial, a report by Davis and Ramsey shows that use of tetrahydrocannabinol (THC) may also help reduce seizures.

*Cannabis* has been shown to be both pro-convulsant (Brust et al., 1992) and anti-convulsant. This study shows that it is not clear if the use of *Cannabis* is a potential risk factor to recreational and medicinal users (Ferdinand et al., 2005).

PCT application WO02/064109 describes a pharmaceutical formulation where the cannabinoids THC and CBD are used.

The application GB091158.9 describes the use of THCV for the treatment of generalized seizures.

The onset of epileptic seizures can be life threatening including long-term implications (Lutz, 2004) including mental health problems, cognitive deficits and morphological changes (Swann, 2004, Avoli et al., 2005). The onset of epilepsy also greatly affects lifestyle as suffers live in the fear of consequential injury or the inability to perform daily tasks (Fisher et al., 2000)

The present invention identifies a novel drug combination that will enhance or otherwise offer benefits in the use of certain SAEDs.

SUMMARY OF THE INVENTION

The invention provides a composition for treating seizure disorders such as epilepsy comprising: (i) an anticonvulsant drug of the hydantoin family such as phenytoin; (ii) phytocannabinoid cannabidiol (CBD); and (iii) a fat-soluble vitamin such as vitamin A. The composition can also include a water-soluble vitamin such as folic acid to reduce side effects and boost metabolism.

The invention also provides a composition for decreasing the metabolic side effects of CBD and increasing its bioavailability to a patient by combining CBD and a fat-soluble vitamin like vitamin A in an amount that produces the desired effect.

The invention also provides a method for treating seizure disorders in mammals such as epilepsy by administering to a subject in need thereof a composition including: (i) an effective amount of an anticonvulsant drug of the hydantoin family; (ii) phytocannabinoid cannabidiol (CBD) in a dosage amount sufficient to inhibit degradation of said anticonvulsant drug; and (iii) a fat-soluble vitamin in an amount effective to inhibit degradation of said anticonvulsant drug and CBD thereby increasing the amount of bioavailable anticonvulsant drug and CBD to said patient. A water-soluble vitamin like folic acid can be administered separately to reduce side effects or it can be included in the composition.

DETAILED DESCRIPTION OF THE PREFERRED EMBODIMENT(S) OF THE INVENTION

Hydantoin drugs such as Dilantin induce the cytochrome P450 hepatic enzyme system. It is believed that this is responsible for the degradation and/or metabolism of CBD and the first pass metabolism of Dilantin. Using a higher dose of CBD in combination with a fat-soluble vitamin like vitamin A is believed to overcome the metabolic effect of cytochrome p450 enzyme and increase the bioavailability of Dilantin and CBD. The combination of CBD and vitamin A in combination with a lower dose of standard Dilantin to relieve multiple types of seizure disorder and epilepsy and obtain the desired cumulative anticonvulsant effect and reduced side effects of Dilantin could not be anticipated.

Anticonvulsant hydantoins that can be used in the invention are selected from the group of ethotoin, fosphenytoin, mephenytoin and phenytoin. Each is available commercially under various brand names: Dilantin and Epanutin (phenytoin); Peganone (ethotoin); Mesantoin (mephenytoin); and Cerebyx (fosphenytoin).

Phenytoin is believed to protect against seizures by causing voltage-dependent block of voltage gated sodium channels. This blocks sustained high frequency repetitive firing of action potentials. This is accomplished by reducing the amplitude of sodium-dependent action potentials through enhancing steady state inactivation. Sodium channels exist in three main conformations: the resting state, the open state, and the inactive state.

Phenytoin binds preferentially to the inactive form of the sodium channel. Because it takes time for the bound drug to dissociate from the inactive channel, there is a time dependent block of the channel. Since the fraction of inactive channels is increased by membrane depolarization as well as by repetitive firing, the binding to the inactive state by phenytoin sodium can produce voltage-dependent, use-dependent and time-dependent block of sodium-dependent action potentials.

The primary site of action appears to be the motor cortex where spread of seizure activity is inhibited. Possibly by promoting sodium efflux from neurons, phenytoin tends to stabilize the threshold against hyper excitability caused by excessive stimulation or environmental changes capable of reducing membrane sodium gradient. This includes the reduction of post-tetanic potentiation at synapses, which prevents cortical seizure foci from detonating adjacent cortical areas. Phenytoin reduces the maximal activity of brain stem centers responsible for the tonic phase of generalized tonic-clonic seizures.

Other hydantoins used in the invention have similar mechanisms of action.

Cuttle et al, in Drug Metab. Dispos. 2000 August; 28(8): 945-50 have reported that phenytoin provokes a skin rash in 5 to 10% of patients receiving the drug for the treatment of seizures and other disorders. Cytochrome P450 enzymes metabolize phenytoin. Reactive drug metabolites are believed to cause covalent modification of normal self proteins by which can bring about a skin rash. Patients treated according to the invention with reduced amounts of hydantoin drug will experience fewer incidents of skin rash.

CBD can be used in its pure form or as a mixture of compounds that result from extracting *Cannabis* plants. Such mixtures contain CBD, THC or tetrahydrocannabinol (which in turn is a mixture comprising 9-tetrahydrocannabinol (delta-9 THC), 8-tetrahydrocannabinol (delta-8 THC) and 9-THC Acid), Cannabinol (CBN), Cannabichromene (CBC), Cannabigerol (CBG), terpenoids and flavonoids.

The preferred CBD mixture is extracted from a *Cannabis indica*, the composition of which is known. The use of CBD from *Cannabis indica*, which can contain up to 50% THC (based on the amount of CBD), is preferred. See, for example, Qureshi et al. (World Applied Sciences Journal; 2012; 19 (7): 918-923, ISSN 1818-4952, IDOSI Publications) disclosing a *Cannabis indica* extract containing 54% CBD and 24% THC. Preferred mixtures for use in the invention contain at least 50% by weight CBD wherein the weight ratio of CBD to THC is at least 2:1, preferably at least 3:1.

The preferred CBD mixture is extracted from a *Cannabis indica* dominant strain, or a hybrid *Cannabis indica* and *Cannabis sativa* strain, using high pressure and carbon dioxide as a solvent in a 1500-20 L subcritical/supercritical $CO_2$ system using a Super Critical Systems, for example made by Apeks, 14381 Blamer Rd., Johnstown, Ohio, 43031. See http://www.apekssupercritical.com/botanical-extraction-systems/.

Apeks Systems, as an example, use valve less expansion technology with no constrictions or regulating valves to cause clogging in the system between the extraction vessel and the CO2 expansion separator. Flow of liquid $CO_2$ and dissolved oil travels from the extraction vessel into the separator, and the oil is separated from the $CO_2$ in the separator/collection vessel. $CO_2$ is recycled during the extraction process and recovered and regenerative heat capture methods are used to increase efficiency.

A further process using solvents can be used to remove THC from the mixture leaving either pure CBD or so-called "organic CBD" containing CBD, CBN, CBC, CBG CBN, terpenoids and flavonoids. The use of essentially THC-free Organic CBD from *Cannabis indica* is more preferred.

Another source of CBD essentially free of THC is the CBD mixture obtained from hemp or by extracting hempseed oil. See Leizer et al, J. Nutraceuticals, Functional and Medical Foods, Vol. 2(4) 2000, The Haworth Press, Inc. Elixinol (D&G Health LLC) is a predominantly CBD product extracted from hempseed oil that contains trace amounts of THC.

The preferred blocking compound is a natural or synthetic fat-soluble vitamin normally stored in fatty tissue such as vitamins A, D, E and K.

Vitamin A is a fat-soluble group of unsaturated compounds that includes retinol, retinal, retinoid acid, beta-carotene and other provitamin A carotenoids. Vitamin A is preferred because it is less likely to interact with other medications.

Vitamin D is a fat-soluble secosteroid such as cholecalciferol and ergocalciferol.

Vitamin E is commonly gamma-tocopherol from corn or soybean oil, or alpha-tocopherol from wheat germ oil or sunflower and safflower oils.

Vitamin K is synthesized by plants and is a family 2-methyl-1,4-naphthoquinone (3-) derivatives.

Natural or synthetic water-soluble vitamins can be used to reduce side effects and boost the immune system and include folic acid, folate, vitamin B9 and vitamin B12.

The preferred water-soluble vitamin is folic acid, which is the synthetic form of vitamin B also known as pteroylglutamic acid.

Patients who are subject to seizure disorders such as epilepsy, and skin rashes, are treated to control and reduce the frequency of seizures and skin rashes by administering the drug combination described above in accordance with further details of the invention, which are disclosed herein.

Patients being treated for seizure disorders usually receive an anticonvulsant drug such as phenytoin in amounts of about 10 to as much as 20 mg/kg of patient weight per day. Because of the P450 blocking effect provided by a fat-soluble vitamin, the bioavailability of hydantoin drugs and CBD is increased which allows the use of lesser amounts of a hydantoin drug with a concomitant lowering in undesirable side effects normally seen with drugs like phenytoin, especially fewer skin rashes. Thus, it is preferred to use hydantoin dosages of about 30% less that the normal dosage when the drug is given alone, or from about 7 to about 14 mg/kg of patient body weight, and more preferably not more than about 7 mg/kg of patient body weight per day.

The dosage amount of CBD to be used with the anticonvulsant drug is from about 0.5 to about 1.0 mg/kg of patient weight.

Another embodiment of this invention is a composition for decreasing the metabolic side effects of CBD and increasing its bioavailability to a patient by combining CBD and a fat-soluble vitamin like vitamin A in an amount that produces the desired effect, for example from about 0.5 to about 1.0 mg/kg patient body weight. In this embodiment, it is expected that the therapeutic dosage of CBD can be reduced by 10 to 30%.

The dosage of fat-soluble vitamin, especially vitamin A, is about 100 IU to about 2000 IU per kg of patient body weight per day.

A water-soluble vitamin, especially folic acid, can be administered separately at from about 1 to about 20 mg/day or compounded with the other components in a dosage amount of about 0.5 to about 1.0 mg/kg of patient weight.

Candidates to be treated according to the invention will generally present with symptoms or signs associated with seizure disorders such as recurrent loss of consciousness, recurrent seizures and/or a prior diagnoses of medically refractory epilepsy. The invention is especially useful in treating patients who have had recurrent and/or poorly controlled seizures or epilepsy in spite of being treated with one or more know anticonvulsant drugs.

The expected response in patients treated according to the invention is a reduction in seizure intensity and/or frequency once a steady state of the active pharmaceutical components is achieved. Up to 14 or more days of treatment may be required before benefits are achieved. The same applies to patients experiencing skin rashes from taking hydantoin to control seizures.

Patients with allergies, cardiac rhythm disturbances, metabolic syndrome or a history of *Cannabis* abuse are not candidates to be treated according to the invention.

Animals, especially dogs and cats, can be treated according to the invention. Seizures in dogs and cats are caused by abnormal brain activity; they can to subtle or cause violent convulsions. Some seizures only occur once but repeated seizures require treatment to prevent larger areas of the brain from becoming affected. Dosage amounts and serum levels of drug are the same as disclosed above for human patients.

While this invention has been described as having preferred sequences, ranges, ratios, steps, order of steps, materials, structures, symbols, indicia, graphics, color scheme(s), shapes, configurations, features, components, or designs, it is understood that it is capable of further modifications, uses and/or adaptations of the invention following in general the principle of the invention, and including such departures from the present disclosure as those come within the known or customary practice in the art to which the invention pertains, and as may be applied to the central features hereinbefore set forth, and fall within the scope of the invention and of the limits of the claims appended hereto or presented later. The invention, therefore, is not limited to the preferred embodiment(s) shown/described herein.

What is claimed is:

1. Composition for treating a seizure disorder of a patient in need of such treatment, comprising:
   (i) an anticonvulsant drug of the hydantoin family in an amount of not greater than about 2 mg/kg of the patient's body weight, which is effective to reduce seizure intensity and/or frequency;
   (ii) phytocannabinoid cannabidiol (CBD) in an amount of from about 0.5 to about 1.0 mg/kg of the patient's body weight;
   (iii) a water-soluble vitamin in an amount of about 0.5 to about 1.0 mg/kg of the patient's body weight; and
   (iv) a fat-soluble vitamin.

2. Composition of claim 1 wherein the anticonvulsant drug is selected from the group consisting of ethotoin, fosphenytoin, mephenytoin and phenytoin.

3. Composition of claim 1 wherein CBD is extracted from *Cannabis indica* or *Cannabis sativa* or a hybrid of *Cannabis indica* and *Cannabis sativa*.

4. Composition of claim 1 wherein CBD is synthetic CBD.

5. Composition of claim 1 wherein the fat-soluble vitamin is selected from the group consisting of vitamins A, D, E and K.

6. Composition of claim 1 wherein the fat-soluble vitamin is vitamin A.

7. Composition of claim 1 wherein the fat-soluble vitamin is in an amount effective to inhibit degradation of the anticonvulsant drug.

8. Composition of claim 1 wherein the water-soluble vitamin is selected from the group consisting of folic acid, folate, vitamin B9 and vitamin B12.

9. Composition of claim 8 wherein the water-soluble vitamin is folic acid.

10. Composition of claim 1 wherein the fat-soluble vitamin is in an amount of about 100-2000 IU/kg of the patient's body weight.

11. Composition for treating a seizure disorder of a patient in need of such treatment, comprising:
    (i) an anticonvulsant drug of the hydantoin family in an amount of not greater than about 7 mg/kg of the patient's body weight, which is effective to reduce seizure intensity and/or frequency;
    (ii) phytocannabinoid cannabidiol (CBD) in an amount of from about 0.5 to about 1.0 mg/kg of the patient's body weight;
    (iii) a water-soluble vitamin in an amount of about 0.5 to about 1.0 mg/kg of the patient's body weight; and
    (iv) a fat-soluble vitamin in an amount of about 100-2000 IU/kg of the patient's body weight.

12. Composition of claim 11 wherein the anticonvulsant drug is selected from the group consisting of ethotoin, fosphenytoin, mephenytoin and phenytoin.

13. Composition of claim 11 wherein CBD is extracted from *Cannabis indica* or *Cannabis sativa* or a hybrid of *Cannabis indica* and *Cannabis sativa*.

14. Composition of claim 11 wherein CBD is synthetic CBD.

15. Composition of claim 11 wherein the amount of CBD is sufficient to inhibit degradation of the anticonvulsant drug.

16. Composition of claim 11 wherein the fat-soluble vitamin is selected from the group consisting of vitamins A, D, E and K.

17. Composition of claim 11 wherein the fat-soluble vitamin is vitamin A.

18. Composition of claim 11 wherein the fat-soluble vitamin is in an amount effective to inhibit degradation of the anticonvulsant drug.

19. Composition of claim 11 wherein the water-soluble vitamin is selected from the group consisting of folic acid, folate, vitamin B9 and vitamin B12.

20. Composition of claim 19 wherein the water-soluble vitamin is folic acid.

21. Composition of claim 11 wherein the seizure disorder is epilepsy.

22. Composition of claim 1 wherein the seizure disorder is epilepsy.

23. Method for treating a patient having a seizure disorder, comprising administering the composition of claim 1 to the patient.

24. Method of claim 23 wherein the seizure disorder is epilepsy.

25. Method for treating a patient having a seizure disorder, comprising administering the composition of claim 11 to the patient.

26. Method of claim 25 wherein the seizure disorder is epilepsy.

* * * * *